United States Patent
Ma et al.

(10) Patent No.: US 6,280,500 B1
(45) Date of Patent: *Aug. 28, 2001

(54) METHODS FOR REMOVING POLLUTANTS FROM CONTAMINATED SOIL MATERIALS WITH A FERN PLANT

(75) Inventors: Lena Q. Ma; Ken M. Komar, both of Gainesville; Elizabeth D. Kennelley, Archer, all of FL (US)

(73) Assignee: University of Florida, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/471,566

(22) Filed: Dec. 23, 1999

Related U.S. Application Data

(60) Provisional application No. 60/129,203, filed on Apr. 14, 1999.

(51) Int. Cl.[7] .................. C22B 3/18; C22B 3/24
(52) U.S. Cl. .................. 75/711; 75/710; 75/712; 210/602; 47/58.1; 800/295
(58) Field of Search .................. 800/260, 278, 800/295, 276; 75/711, 712; 210/602, 681, 682

(56) References Cited

U.S. PATENT DOCUMENTS

| | | | |
|---|---|---|---|
| 5,000,852 | * | 3/1991 | Tel-Or et al. .................. 210/602 |
| 5,785,735 | * | 7/1998 | Tel-Or et al. .................. 210/602 |
| 5,809,693 | * | 9/1998 | Chet et al. .................. 47/58 |

OTHER PUBLICATIONS

Ho et al. Bull. Environ Contam. Toxicol. vol, 35, pp. 430–438, 1985.*

Noctor et al. Journal of Experimental Botany, vol. 49, No. 321, pp. 623–647, Apr. 1998.*

* cited by examiner

*Primary Examiner*—Amy J. Nelson
*Assistant Examiner*—Medina A. Ibrahi
(74) *Attorney, Agent, or Firm*—Brian S. Steinberg; Law Offices of Brian S. Steinberg

(57) ABSTRACT

The subject invention provides materials and methods for remediating soil and/or water which has been contaminated with arsenic, phosphorous, or other metals. In a preferred embodiment, the subject invention provides fern plants which accumulate arsenic from contaminated soils. The fern plants efficiently remove arsenic from the soil. The fern plants can be harvested and readily disposed of, or can be treated to recover arsenic.

33 Claims, No Drawings

METHODS FOR REMOVING POLLUTANTS FROM CONTAMINATED SOIL MATERIALS WITH A FERN PLANT

CROSS-REFERENCE TO RELATED APPLICATIONS

This application claims priority from provisional application U.S. Ser. No. 60/129,203, filed Apr. 14, 1999.

BACKGROUND OF THE INVENTION

Arsenic is a major contaminant of soils, sediments, wastes, and water in the United States and in foreign countries. Contamination of soils results from, for example, pesticides and wood treatments. Not only is arsenic a prevalent contaminant but it is also particularly dangerous because it is a known carcinogen. Currently there is no cost effective and efficient way to clean up soils contaminated with arsenic.

The use of arsenic in agricultural and industrial processes has resulted in numerous contaminated soils in Florida. During the early part of the 20$^{th}$ century, arsenic was commonly used as an insecticide component to control disease-carrying ticks on southern cattle so that Florida cattlemen could sell to the northern cattle markets. Arsenic, typically in the form of arsenic pentoxide, was also used in conjunction with copper sulfate and sodium or potassium dichromate as a wood preservative which is known as the copper/chromium/arsenic wood preservative process, or CCA (Grant and Dobbs 1977). With both of these processes, the risk of soil contamination from spills and leaks was great. The arsenic level at many of these sites is currently higher than 600 mg kg$^{-1}$ even after years of idleness. The typical concentration range in soil is between 0.1 to 40 mg kg$^{-1}$ with a mean concentration of 5-6 mg kg$^{-1}$ (Kabata-Pendias and Pendias, 1992). The typical range of arsenic in Florida soils is 0.01 to 6.1 mg kg$^{-1}$ (Ma et al. 1997).

Thus, environmental arsenic contamination is of concern due to its biological activities as a teratogen, carcinogen, and mutagen as well as its detrimental effects on the immune system (Squibb and Fowler 1983). Efforts to remediate these arsenic contaminated soils have been minimal, primarily due to the lack of technologies and the costs associated with the excavation and landfilling of the soil materials.

In most soil systems, arsenic is present in many forms of which arsenate is typically the dominant one. In this form, it has properties very similar to phosphate including the formation of insoluble salts with cations and sorption by soil constituents. Because arsenic has a wide range of oxidation states (−3,0,+3, and +5) it has the ability to form many types of organic and inorganic complexes. At high pH ranges, typically 7 to 9, the arsenic in soils predominantly consists of complex oxyanions of As(V), such as $AsO_2$—, $AsO_4^{-3}$, $HAsO_4^{-2}$, and $H_2AsO_4^{-1}$. In soils with low pH and low Eh, the predominant forms of arsenic are the arsenites ($H_3AsO_3$) (Kabata-Pendias and Pendias, 1992).

Although arsenic is commonly found in all natural systems at minute levels, it can be very toxic to both plants and animals at higher concentrations. The toxic effects of arsenic have been known for some time. The exposure of animals to arsenic is second in toxicity only to lead for many farm and household animals. Most cases of arsenic poisoning in animals occur in bovine and feline species as a result of contaminated feed supplies. Other species that are affected are forage-eating animals, such as horses and sheep, that encounter fields that may have been treated with arsenic pesticides. The toxic effects of arsenic to humans and animals can be related to the interactions that occur within the cells of poisoned individuals, especially the mitochondria.

Arsenic is present naturally in almost all plant and tree species in minute amounts. The tolerance of plant and tree species to arsenic varies with species, soil type, and the form of arsenic present in a soil (Porter and Peterson, 1977). Over time, a classification scheme was developed to identify the tolerance of vegetables and fruit species (Table 1). In general, the distribution of arsenic in the plant species follows a common trend. Typically, the roots will contain higher concentrations of arsenic than the stems, leaves, and fruits. Some plant species have demonstrated the ability to accumulate elevated arsenic in the above ground portion of the plants. Porter and Peterson (1977) identified that some species in the Agrostis genus had the ability to accumulate up to 3,460 mg kg$^{-1}$ As from soil that contained up to 2.6% arsenic. Other reports have demonstrated the ability of Douglas fir, *Pseudotsuga menziesii*, to accumulate up to 10,000 mg kg$^{-1}$ As in ash, allowing this tree to be used as a biogeochemical indicator for gold, silver, and other ores (Fowler, 1977; Cullen and Reimer, 1989).

TABLE 1

Arsenic Tolerance of Agronomic Crops

| Tolerance Grouping | Crop Species |
| --- | --- |
| Very Tolerant | Asparagus, potato, tomato, carrot, tobacco, dewberry, grape, red raspberry |
| Fairly Tolerant | Strawberry, sweet corn, beet, squash |
| Low or No Tolerance | Snap pea, lima bean, onion, pea, cucumber, alfalfa |

Source: Walsh and Keeney (1975)

Due to the concern expressed over arsenic contaminated sites, various remediation techniques have been developed. Methods for remediating arsenic contaminated soil can be performed in situ and ex situ and have varying degrees of complexity, effectiveness, and cost. These methods can be divided into three techniques: chemical, physical, and biological remediation methods.

One of the biological remediation techniques is phytoremediation. Phytoremediation is a growing technology that utilizes the ability of plants to accumulate nutrients and trace elements. Phytoremediation is the process of employing plants to remediate contaminated soils. Typically this is done in one of two ways, either by phytostabilization or by phytoextraction (Bolton and Gorby 1995). With phytostabilization, plants are used to stabilize contaminated soils by decreasing wind and water erosion as well as decreasing water infiltration and contaminant leaching into groundwater. Phytoextraction attempts to remove contaminants from the rhizosphere through plant uptake and the contaminants are accumulated in roots, leaves and/or stems. The plant materials are then harvested and the contaminants reclaimed from the plant biomass or the materials are disposed of at a hazardous waste facility.

Currently, certain plants have been identified that can be utilized to remediate soil and water systems contaminated with metals, metalloids, petroleum constituents, pesticides, and industrial wastes (Dix et al., 1997; Ebbs et al., 1997; Lasat et al., 1998). Also, many plant species have been identified that accumulate lead, selenium, nickel, zinc, and other metals. For example, U.S. Pat. Nos. 5,364,451 and 5,711,784 describe phytoremediation of metal-containing soils. McGrath et al. (1997) demonstrated the effective removal of cadmium and zinc by plant species *Thlaspi caerulescens*. Kramer et al. (1997) found that *Thlaspi goesingense* (Halacsy) removes nickel from contaminated soils.

For remediation of contaminant sites and/or recovery of precious metals, phytoextraction can be an attractive option. Phytoextraction is the process of removing a contaminant from a system via plant roots for remediational purposes. Originally, the term phytoextraction was applied to the removal of trace elements from soils, but recently new applications have been discovered for this process. One of the newest uses of phytoextraction has been its use in accumulating trace elements of economic value, such as gold and nickel.

In some situations, soil amendments and chelating agents can be used to aid in plant growth and in accumulation of trace elements by plants. The soil may have a low pH, poor aeration, inappropriate soil texture, high salinity, etc. To overcome this, agronomic techniques can be used to increase the chance of plant survival. These include addition of organic matter, liming, and fertilization to name a few. In certain situations, addition of soil amendments decreases the quantity of the contaminant that the plant will accumulate but this is typically offset by the increase in biomass that is produced (Bennett, 1998).

For many soil contaminants, chelating agents or organic acids are required to assist in their accumulation by plants. The low solubility of many trace elements and radionuclides is often the limiting factor in metal extraction by plants (Huang et al., 1998). For example, lead in soil has a limited solubility and low bioavailability for plant uptake due to complexation with organic matter, sorption on clay and oxides, and precipitation as carbonates, hydroxides, and phosphates.

To overcome this problem, metal-chelating agents can be added. Traditionally, chelates were used in agriculture and horticulture to deliver micronutrients to plants. With the use of chelates in phytoremediation, the chelate is used to increase the bioavailability of the contaminant for plant uptake. There are concerns with the use of chelates though. In some situations, the chelate may have a detrimental effect on plant growth. In one experiment, lead hyperaccumulating plants were grown in contaminated soils for two weeks before the chelating agent EDTA was applied. After one week, the plants were harvested after sustaining significant damage (Cunningham et al., 1997). Other experiments utilizing EDTA to increase the bioavailability of lead for phytoextraction have shown a significant increase in the accumulation of lead by even common agronomic plants.

There are other concerns associated with the use of chelates, in addition to the possible detrimental effect on plant health. Much concern has been expressed over the potential of groundwater contamination. The use of chelates will also increase the cost of a remediation process. Some estimates state that to increase the mobility of one ton of lead in contaminated soil will require approximately one ton of EDTA.

Prior to the subject invention, there has been no plant species identified that can accumulate large quantities of arsenic into its biomass. Also, prior to the subject invention there has been no report of the use of ferns in phytoremediation.

BRIEF SUMMARY OF THE INVENTION

The subject invention pertains to the identification of plants which are able to extract pollutants from contaminated materials. In a preferred embodiment, the pollutant is arsenic. Pollutants can be removed from materials including, but not limited to, soils, sediments, wastes, ash, and water by the plants of the subject invention which accumulate the pollutants in the biomass of the plant. This is advantageous because these plants can be used to efficiently remediate materials which have been contaminated.

In a preferred embodiment the subject invention provides a method for remediating arsenic-contaminated materials wherein arsenic accumulating ferns remove arsenic from the soil. Specifically exemplified herein is the use of the Chinese ladder brake fern (*Pteris vittata*). Advantageously, this species can have a total accumulation of arsenic that exceeds 2,000 mg kg$^{-1}$ on a dry weight basis.

The fern plants of the subject invention accumulate arsenic in very high concentrations. The plant leaves, stems, and/or roots can then be harvested and readily disposed of, thereby reducing the arsenic content of the contaminated soil. Alternatively, arsenic may be recovered from the harvested plants.

The fern plants of the subject invention have many advantageous characteristics for use in phytoremediation. For example, these plants are extremely efficient in extracting arsenic from soils (extremely high arsenic enrichment factor), they grow in many environments, they grow quickly producing a large biomass and they reproduce easily. Also, advantageously, they are perennials which do not need to be replanted each year.

DETAILED DESCRIPTION OF THE INVENTION

The subject invention pertains to the identification of plants that accumulate arsenic in very high concentrations. These plants can be used to remediate soils which are contaminated with arsenic. Plants can also be used according to the subject invention to remove phosphorous from contaminated sites. Preferably, the plants which are used in the remediation methods of the subject invention are fern plants. With the teachings provided herein, the person skilled in the art could, for the first time, utilize ferns to remove various inorganic pollutants, including metals, from contaminated materials. The inorganic pollutants may be bonded to, or other wise chemically associated with, an organic compound. The metals may be, for example, lead, gold, selenium, copper, cadmium, chromium, nickel, or zinc. Preferably, arsenic is removed. The material from which the pollutant is removed may be, for example, soil, sediment, waste, ash, or water.

In a preferred embodiment, the method of the subject invention involves contacting a fern plant with arsenic-containing soil and maintaining the plant in the soil environment under conditions sufficient for the plant to accumulate arsenic from the soil. The plant is maintained in the soil for a time and under conditions sufficient for the plant to accumulate arsenic in the stems, leaves and/or roots. The plant may be harvested from the soil and disposed of.

Arsenic "accumulating" plants refer to the ability of the plants described herein to perform one, or more, of the following activities: (i) transporting arsenic from soil particles and/or liquid into the roots and/or other tissues; (ii) physical and/or chemical sorption of arsenic to the root biomass; and (iii) prevention or inhibition of leaching of arsenic from the soil environment. In a preferred embodiment arsenic is transported into the leaf and/or stem tissue of the fern. Phosphorous "accumulating" plants have one or more of the above-listed characteristics with respect to phosphorous.

As used herein, reference to "ferns" includes the Pteridophytes (true ferns). Most ferns are sporophytes which reproduce by means of spores. Ferns typically produce masses of sporangia either on the underside of vegetative leaves or on specialized leaves that function only as reproductive structures. Specifically exemplified herein are ferns of the family Pteridaceae. The Pteris ferns are also known as brake ferns. Specifically exemplified herein are the *P. vittata* ferns.

Ferns useful according to the subject invention can be readily identified by those skilled in the art. Useful guides to ferns are readily available and include, for example, Lakela, Olga and Robert W. Long; "*Ferns of Florida*, An Illustrated Manual and Identification Guide" [1976], Banyan Books, Miami, Fla.); Jones, David L. (Encyclopedia of Ferns [1987], Lothian Publishing Company PTY LTD); and Snyder, Jr., Lloyd H. and James G. Bruce (Field Guide to the Ferns and Other Pteridophytes of Georgia" [1986] The University of Georgia Press).

Advantageously, the ferns used in the present invention: (a) can be grown to high biomass; (b) are adaptable for growth in various agroclimatic conditions; (c) are adaptable to high-density culture; and (d) are amenable to genetic manipulation by crossing, selection, mutagenesis and/or gene transfer. The excellent remediation properties presented herein are under field conditions and can be improved by optimization of field conditions as described herein, or by performing the remediation process in a controlled environment such as in a greenhouse. The conditions which can be manipulated to optimize performance in a given system include pH, nutrients, and chelators. The pH may be adjusted, for example, to be greater than 6.5. Even pH's of 8–10 or higher can be used. Macronutrients and micronutrients may also be applied including, for example, nitrogen, potassium, and phosphorous. Additionally, chelators such as EDTA, DTPA, NTA, citric acid, and oxalic acid can be applied.

The fern plants specifically exemplified herein are highly useful in removing arsenic from contaminated soils. In an alternative embodiment, the fern plants can be genetically manipulated to improve and/or expand their phytoremediation characteristics. Such characteristics may be for example the growth rate of the ferns, the uptake rate of arsenic, and the hardiness of the plant. The genetic manipulation may be through, for example, traditional breeding techniques, mutagenesis, and/or genetic engineering. In a related embodiment, the genetic components responsible for the ability of ferns to accumulate arsenic can be identified, isolated, and, if desired, transferred to another plant species thereby conferring on the transformed plant the ability to accumulate arsenic in useful levels. Alternatively, microorganisms and/or their genetic components involved in the arsenic removal process can be isolated and utilized.

In a specific embodiment, the subject invention provides an arsenic-accumulating fern plant. This plant has been shown to accumulate over 2,500 mg/kg arsenic (dry weight) in its rachis (stems) and pinna (leaves). The arsenic concentrations in the soil where the plant has been studied range from 19 to 1,603 mg/kg. Thus, this plant has an extraordinary capability to enrich nearly 200 times more arsenic in the plant tissue than in the contaminated soil. Advantageously, the fern plants of the subject invention remove contaminants from soils having even low concentrations of pollutants. This is important for the process of the subject invention to lower the concentration of contaminants to an acceptable level.

The preferred methods of the invention involve growing one or more members of these plants under conditions sufficient for them to accumulate arsenic in their biomass. The term "arsenic" also includes mixtures, or compounds, comprising arsenic and organic or inorganic compounds.

The arsenic-containing environment into which these plants are introduced is not intended to limit the scope of the invention. That is, as long as the environment can sustain growth of ferns, the environment can range from purely aquatic environments (i.e., hydroponic culture) to soil environments of varying degrees of water saturation, organic matter content, mineral content, and the like. Advantageously, ferns can be grown in the sun or in the shade, and in either moist or dry environments. For example, the subject invention may be utilized in wetlands. The pH can be as high as about 8–10 or even higher. It will be appreciated by those of ordinary skill in the art that the term "soil" can, therefore, include a wide variety of chemical and physical types. Thus, the materials from which pollutants can be removed according to the subject invention include soil, sediment, waste, ash, and water.

The arsenic-accumulating ferns suitable for the present methods extract arsenic from the environment into the roots of the plant. Preferably, the plants will translocate the arsenic from the roots into the shoots (i.e., the above-ground portions of the plant). The rates of accumulation can vary depending on a variety of factors, including the total arsenic concentration, soil type, pH, moisture content, organic matter content, soil temperature, planting density, and fertilizer use. With the teachings provided herein, the skilled artisan can readily select the preferred conditions for a particular application.

Generally, accumulation by the preferred ferns can be as high as 100-fold or more above levels present in the soil. The most preferred plant members accumulate several percent of arsenic as dry weight of shoot biomass and dried root biomass. Shoots or roots can then be harvested. The ability of the plants of the present invention to accumulate arsenic in the shoots is important because the shoots represent the harvestable (i.e., above-ground) biomass. The accumulation of arsenic in the shoots is preferred because generally roots are more difficult to harvest than shoots when the plants are grown in soil. However, any portion of the plant is potentially harvestable. For example, leaves, stems, fronds and roots may be harvested from fern plants.

In addition to arsenic contaminated soil, fern plant samples were also collected from uncontaminated sites, with arsenic concentrations ranging from 0.5 to 7.6 mg/kg. The arsenic concentrations in the frond (above-ground biomass) of these plants ranged from 12 to 64 mg/kg, with a maximum arsenic enrichment factor of 136. This clearly demonstrates that the fern plants of the subject invention accumulate arsenic from soils containing high as well as low arsenic levels.

Thus, the arsenic enrichment factor of ferns is observed under natural growing conditions in contaminated as well as uncontaminated soils. The person skilled in the art, having the benefit of the current disclosure could optimize conditions for growth of the plants and uptakes of the pollutants. The uptake reported here is under conditions in the field and could be increased in an appropriately controlled environment such as a green house. Arsenic concentrations in common plants range from 0.01 to 5 mg/kg, with an average of 2.5 mg/kg. Thus, the fern plants of the subject invention accumulate as much as 3,000 times more arsenic than the average of common plants without suffering from arsenic toxicity. This is extremely unusual for a plant since arsenic has been used as a herbicide to control weeds.

The fern plants of the subject invention are highly advantageous for use in methods to remove arsenic from contaminated soils. These plants are capable of surviving on a wide range of soil conditions, ranging from limestone surfaces to rocky woodland. These plants also have a relatively large biomass; for example, these plants may produce a frond that is 30–90 cm in length, with blades of 25–60 cm long and 13–25 cm wide. Also, ferns can be easily reproduced in tens of thousands from just one plant. Once planted in an arsenic contaminated soil, the ferns of the subject invention come back every year because they are perennial plants, i.e. the plants can be harvested season after season until the site is cleaned up without reseeding or replanting.

In a specific embodiment, the subject invention concerns an arsenic accumulating Chinese brake fern (*Pteris vittata*). The average arsenic concentration in the soil where samples were collected was 394 mg/kg, with the highest arsenic concentration being 1,603 mg/kg. The average arsenic concentrations from eight plant samples in leaves, stems and roots were 4,359; 1,824; and 1,758 mg/kg dry weight, with the highest arsenic concentration being 7,526 mg/kg in leaves. Based on the average arsenic concentration, the arsenic concentration in the plant was typically at least 5 times greater than that in soil. This plant is highly advantageous for extracting arsenic from arsenic contaminated soil, thus cleaning up the soil.

The arsenic accumulating plants of the subject invention can be used to remediate tens of thousands of arsenic contaminated soils nationwide and around the world. There are up to 10,000 arsenic contaminated sites in Florida alone. This technology is cost-effective and environmentally friendly and can be used by anyone who has to clean up arsenic contaminated soils. The remediation can be conducted in situ in the field or ex situ by removing the material to another location for a more controlled system. When the ferns are harvested, the arsenic, phosphorous or other metal can be recovered or disposed of using methods known to those skilled in the art. The disposed or recovery step may include, for example microbial treatment, chemical treatment, incineration, treatment with other plants, etc. These methods may further include the use of gasifiers as described in WO 99/09115.

Materials and Methods

Site Selection: An abandoned CCA wood preservative site located in central Florida was selected for a study. This site was operated from 1952 until 1962, pressure treating lumber in a cylinder 50 feet long and 6 feet in diameter with an aqueous solution of arsenic pentoxide, copper sulfate, and sodium or potassium chromate. From this activity, the site became heavily contaminated with arsenic, copper, and chromium. The average concentrations for this site are as follows: arsenic was present at a quantity of 575 mg kg$^{-1}$, 84 mg kg$^{-1}$ chromium, and 252 mg kg$^{-1}$ copper (Table 2).

Soil Characterization: Sample grids consisted of 50 by 42-foot plots. Two sample grids that showed high levels of arsenic contamination were sampled. Three soil samples were collected from each site using a bucket auger and combined to give a representative sample. The soil was air dried and then screened to pass through a 2.0-mm sieve and thoroughly mixed before use. Soil pH was determined using 1:2 soil/water ratio and measured on a Fisher Scientific Accumet model 20 pH/conductivity meter. Soil organic matter was determined by the Walkley-Black method. Soil elemental analysis was conducted as follows: Approximately 1.0 g of air-dried soil was weighed into a 20 mL Teflon pressure digestion vessel to which 10 mL of concentrated nitric acid was added. Samples and reagent were mixed, sealed, and digested using a CEM MDS-2000 microwave sample preparation system for 10 minutes at 70 PSI (CEM 1991). Sample solutions were filtered and diluted to a final volume of 100 mL and stored in pre-cleaned polyethylene bottles in a refrigerator before analysis. Analysis for copper, chromium, and arsenic was conducted by graphite furnace atomic absorption on a Perkin Elmer SIMMA 6000 Simultaneous Multielement AA Spectrometer. Phosphorus, potassium, calcium, magnesium, iron, aluminum, and manganese were determined by an inductively coupled plasma spectrophotometer (ICP). These soil characteristics for the arsenic contaminated soil are presented in Table 2.

TABLE 2

| | Soil Characterization of As-Contaminated Site in Central Florida (Mg/Kg) | | | | | | | | |
|---|---|---|---|---|---|---|---|---|---|
| | K | Ca | Mg | Zn | Mn | Fe | Al | P | As |
| Range | 30–300 | 260–37000 | 60–1240 | 8–208 | 6–251 | 836–3670 | 1570–5920 | 40–820 | 39–1603 |
| Mean | 84 | 6346 | 241 | 101 | 45 | 1765 | 3421 | 193 | 361 |

In a specific embodiment the subject invention concerns a method of phytoremediating contaminated materials comprising cultivating ferns in the materials containing contaminants under conditions sufficient to permit the ferns to accumulate contaminants from the materials in the biomass of the ferns such that the contaminants are at least 1% of the air-dried biomass of the ferns. The ferns can then be harvested and the contaminants recovered from the biomass. Preferably, the materials are conditioned to an optimized nutrient level to increase plant biomass and contaminants bioavailability. Sewage, sludge, and compost can be added to promote plant growth. The contaminants include both organic and inorganic pollutants that are of environmental concern and include, but are not limited to, arsenic, phosphorous and other trace elements and heavy metals.

Plant Analysis: Plant tissue samples were collected. The samples were rinsed, dried for 24 hours in a drying room, and ground using a Willey mill. Approximately 1.0 g of dried tree or plant material was weighed into a 20-mL Teflon pressure digestion vessel and mixed with 10 mL of concentrated nitric acid. Tissue samples were digested using a CEM MDS-2000 microwave sample preparation system for 5, 8, and 10 minutes at 40, 80, and 120 PSI respectively (CEM 1991). Sample solutions were diluted to a volume of 100 mL and stored in a refrigerator until analysis by graphite furnace atomic absorption using a Perkin Elmer SIMMA 6000 Simultaneous Multielement AA Spectrometer. Arsenic accumulation in the plant tissue was compared to the level of arsenic present in the soil. This was defined as the accumulation ratio or the phytoremediation coefficient. The results are presented in Table 3.

TABLE 3

Arsenic Levels in Plant and Tree Samples Collected from an As-Contaminated Site (whole plant including leaves, stems, and roots)

| Common Name | Scientific Name | Mean As Concentration in mg kg$^{-1}$ | Accumulation Ratio |
|---|---|---|---|
| Southern Red Cedar | Juniperus silicola | 4.1 | 0.028 |
| Sugarberry | Celtis laevigata | 5.2 | 0.033 |
| Mockernut Hickory | Carya tomentosa | 9.9 | 0.056 |
| White Mulberry | Morus alba | 5.5 | 0.035 |
| Mimosa | Albizia julibrissin | 4.8 | 0.031 |
| Box-elder | Acer negundo | 9.2 | 0.059 |
| Poinsettia | Poinsettia heterophylla | 5.2 | 0.017 |
| Common Ragweed | Ambrosia artemissiiflora L. | 9.4 | 0.051 |
| Goldenrod | Solidaga sp. | 11.2 | 0.061 |
| Beggartick | Bidens alba L. | 8.0 | 0.043 |
| Chinese Ladder Brake Fern | Pteris vittata | 4360 | 23.69 |

Following are examples which illustrate procedures for practicing the invention. These examples should not be construed as limiting. All concentrations are by dry weight and all solvent mixture proportions are by volume unless otherwise noted.

EXAMPLE 1

Accumulation of Arsenic in Ferns A species of arsenic accumulating plant was identified. The species, *Pteris vittata*, demonstrated an average accumulation of 4,360 mg kg$^{-1}$ arsenic in its biomass in dry weight (Table 3). Two further collections of *P. vittata* were made to determine the accumulation of arsenic in the specific plant sections. Samples were collected, rinsed, and dried as before. After drying, the fern samples were separated into root, stem, and leave sections and digested by the previously described methodology. The results are given in Table 4.

TABLE 4

Arsenic Distribution by Plant Section in *P. vittata* in mg kg$^{-1}$

| Collection | Fern Section | Range | Mean |
|---|---|---|---|
| I | Roots | 1152–3103 | 1758 |
| I | Stems | 383–2800 | 1824 |
| I | Leaves | 902–7526 | 4359 |
| II | Fronds | 3480–14540 | 9168 |

EXAMPLE 2
Remediation of Arsenic-contaminated Sites

The use of plants to remediate arsenic contaminated soils in the state of Florida is a feasible and cost effective technique. *P. vittata* is an introduced species that is common to South Africa, Asia, Japan, New Guinea, and Australia (Jones 1987). In the U.S., this species has been identified in Florida, Alabama, and Louisiana. The species can survive on a wide range of soil conditions, preferring to grow in areas that receive plenty of sun, basic soil conditions, and have free drainage. *P. vittata* has been identified growing on limestone formations, masonry mortar, rocky woodlands, canal banks, and often in disturbed sites (Lakela and Long 1976, Snyder and Bruce 1986, Jones 1987). What makes this species so desirable for use in phytoremediating arsenic-contaminated soils is the fact that it produces a significant amount of above ground biomass, having fronds that grow between 30 to 90 cm long, with stipes that are 5 to 30 cm long (Snyder and Bruce 1986). The fact that the largest mean accumulation of arsenic is in this section (mean stem and leaf concentrations of 1824 and 4359 mg kg$^{-1}$ respectively) makes this species highly advantageous for remediation projects. The average arsenic concentration in the leaves was found to be 2 times or more greater than in the roots.

EXAMPLE 3

Identification of Arsenic-Accumulating Plants in Contaminated and Non-Contaminated Sites As shown in Tables 5–9, plants which accumulate arsenic can be found at various locations including contaminated and non-contaminated sites.

TABLE 5

A CCA contaminated soil from Archer, FL

| | Arsenic concentrations | | | | Arsenic enrichment factor | | |
|---|---|---|---|---|---|---|---|
| Sample # | Leaves | Roots | Stems | Soil | Leaves | Roots | Stems |
| 2 | 902 | 2474 | 2800 | 18.8 | 48 | 132 | 149 |
| 3 | 1605 | 1152 | 1387 | 104 | 15 | 11 | 13 |
| 5 | 4548 | 3103 | 2745 | 66.1 | 69 | 47 | 42 |
| 6 | 3186 | 1851 | 2222 | 1603 | 2 | 1 | 1 |
| 7 | 3810 | 2576 | 1998 | 954 | 4 | 3 | 2 |
| 8 | 6236 | 1299 | 383 | 62.4 | 100 | 21 | 6 |
| 9 | 7060 | 1607 | 1909 | 308 | 23 | 5 | 6 |
| 10 | 7526 | N/A | 1152 | 38.9 | 193 | N/A | 30 |
| Mean | 4359 | 1758 | 1824 | 394 | 11 | 4 | 5 |

N/A = Not available.

TABLE 6

Arsenic concentrations in the fern growing in CCA and artificially contaminated soil (ppm)

| Treatment | 2 Weeks | 6 Weeks | 8 Weeks |
|---|---|---|---|
| Control (~6) | 755 | 438 | 539 |
| CCA (~400) | 3,525 | 6,805 | 5,519 |
| 50 ppm | 5,131 | 3,215 | 4,120 |
| 500 ppm | 7,849 | 21,290 | 13,961 |
| 1500 ppm | 15,861 | 22,630 | |

TABLE 7

Arsenic concentration in CCA and artificially contaminated soil after growing the fern for 8 weeks (ppm)

| Treatment | 2 Weeks | 6 Weeks | 8 Weeks | % Reduction |
|---|---|---|---|---|
| CCA | 489 | 361 | 272 | 44.4 |
| 50 ppm | 48.1 | 24.1 | 29.9 | 38.0 |
| 500 ppm | 519 | 317 | 218 | 58.0 |
| 1500 ppm | 1932 | 657 | 258 | 86.6 |

TABLE 8

Arsenic concentrations in different fern species growing in CCA and artificially contaminated soil (ppm)

|  | Control | As = 245 | | | As = 50 | | | As = 500 | | |
| --- | --- | --- | --- | --- | --- | --- | --- | --- | --- | --- |
|  |  | wk 2 | wk 4 | wk 8 | wk 2 | wk 4 | wk 8 | wk 2 | wk 4 | wk 8 |
| Fern 4 | 0.46 | 9 | 33 | 28 | 22 |  | 85 | 3735 |  | 948 |
| Fern 1 | 0.36 | 19 | 18 | 20 | 165 |  | 154 | 1696 |  | 4767 |
| Fern 5 | 0.64 | 61 | 1355 | 2046 | 1542 | 1248 | 2036 | 2919 |  | 1445 |
| Fern 3 | 1.10 | 86 | 2213 | 1114 | 2201 | 5626 | 3847 | 4995 |  | 2448 |
| Fern 2 | 0.54 | 270 | 2165 | 1268 | 3338 | 3802 | 2308 | 6617 |  | 4405 |

TABLE 9

Non arsenic contaminated soil materials from 9 different locations at the University of Florida

| | Arsenic concentrations | | Arsenic enrichment factor |
| --- | --- | --- | --- |
| Sample # | Frond | Soil | Frond |
| 1 | 64 | 0.47 | 136 |
| 2 | 11.8 | 3.65 | 3 |
| 3 | 13.28 | 1.68 | 8 |
| 4 | 42.1 | 2.37 | 18 |
| 5 | 0 | 0.27 | 0 |
| 6 | 38.4 | 2.84 | 14 |
| 7 | 16.2 | 7.56 | 2 |
| 8 | 45.1 | 2.95 | 15 |
| 9 | 33.8 | 0.84 | 40 |

EXAMPLE 4
Accumulation of Phosphorous by Ferns

TABLE 10

Phosphorous Distribution by Plant Section in *P vittata* in mg/kg

| Fern Section | Range | Mean | Enrichment Factor |
| --- | --- | --- | --- |
| Roots | 570–2990 | 1307 | 7 |
| Stems | 220–2810 | 1631 | 8 |
| Leaves | 1340–2400 | 1851 | 10 |
| Soil | 40–820 | 193 | |

Phosphorous enrichment factors ranged from 7 to 10.

TABLE 11

Phosphorus Concentrations in Soil and the Fern from the CCA Site in mg/kg

| | P Concentration | | | | Enrichment Factor | | |
| --- | --- | --- | --- | --- | --- | --- | --- |
| Sample # | Leaves | Roots | Stems | Soils | Leaves | Roots | Stems |
| 2 | 2340 | 920 | 745 | 60 | 39 | 15 | 12 |
| 3 | 2180 | 1980 | 1880 | 40 | 55 | 50 | 47 |
| 5 | 2400 | 2990 | 2810 | 80 | 30 | 37 | 35 |
| 6 | 2220 | 570 | 220 | 180 | 12 | 3 | 1 |
| 7 | 2170 | 1400 | 2590 | 130 | 17 | 11 | 20 |
| 8 | 1340 | 675 | 2610 | 80 | 17 | 8 | 33 |
| 9 | 2180 | 1920 | 2200 | 155 | 14 | 12 | 14 |
| 10 | 2900 | N/A | 3220 | 820 | 4 | N/A | 4 |

N/A = Not available.

As shown in Table 11, the ferns were shown to be effective in accumulating phosphorous.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A process for removing a pollutant from a contaminated soil material wherein said process comprise the steps of:
    planting a fern plant of the family Pteridaceae on said soil material having arsenic as said pollutant;
    wherein substantial concentrations of the arsenic within biomass of the fern plant accumulate solely by phytoremediation such that the fern plant removes said arsenic from said soil material.

2. The process according to claim 1, wherein said soil material inorganic pollutant further contains an additional pollutant selected from the group consisting of metals, trace elements, and phosphorous.

3. The process, according to claim 2, wherein said, additional pollutant is selected from the group consisting of phosphorous, lead, gold, selenium, copper, cadmium, chromium, nickel, and zinc.

4. The process, according to claim 1, wherein said pollutant is chemically associated with, an organic compound.

5. The process according to claim 1, wherein said soil material is selected from the group consisting of sediment in said soil, waste in said soil, ash in said soil, and water in said soil.

6. The process according to claim 5, wherein said soil material is the water in said soil.

7. The process according to claim 5, wherein said soil material is the ash in said soil.

8. The process according to claim 1, wherein said substantial concentrations are an amount that exceeds about 100 mg/kg on dry weight basis.

9. The process according to claim 8, wherein said substantial concentrations are an amount that exceeds about 1000 mg/kg on dry weight basis.

10. The process according to claim 1, wherein said substantial concentrations are at least 2 times greater than the concentration of the arsenic in the soil material from which the arsenic is being removed.

11. The process, according to claim 10, wherein said substantial concentrations are at least 25 times greater than the concentration of the arsenic in the soil material from which the arsenic is being removed.

12. The process, according to claim 1, wherein the concentration in the soil material from which the arsenic is being removed is greater than 10 milligrams per kilogram.

13. The process, according to claim 12, wherein the concentration in the soil material from which the arsenic is being removed is greater than 50 milligrams per kilogram.

14. The process, according to claim 12, wherein the concentration in the soil material from which the arsenic is being removed is at least about 500 milligrams per kilogram.

15. The process, according to claim 1, further comprising the steps of:

removing the arsenic from at least a portion of said fern plant by harvesting, disposing of, or treating said portion of said fern plant to recover said arsenic.

16. The process according to claim 15, wherein said treating is selected from the group consisting of microbial treatment, chemical treatment and incineration.

17. The process, according to claim 15, wherein said portion of said fern is selected from the group consisting of leaves, stems, fronds, and roots.

18. The process, according to claim 17, wherein said portion of said plant is the fronds.

19. The process, according to claim 1, wherein said fern plant is a *P. Vittata*.

20. The process, according to claim 1, wherein said process is conducted in the field.

21. The process, according to claim 20, wherein said process is conducted in a wetlands.

22. The process, according to claim 1, wherein said process is carried out in a greenhouse.

23. The process, according to claim 1, wherein said soil material has a pH of greater than 6.5.

24. The process according to claim 23, wherein said soil material has a pH of greater than 8.

25. The process according to claim 1, wherein said process further comprises prior to said planting the step of:

adding to said material a component which enhances the ability of said fern plant to accumulate said arsenic.

26. The process according to claim 25, wherein said component is selected from the group consisting of pH adjusters, potassium, nitrogen, phosphorous, and chelators.

27. The process according to claim 25, wherein said chelators is selected from the group consisting of EDTA, DTPA, NTA, citric acid, and oxalic acid.

28. The process according to claim 1, wherein said process further comprises prior to said planting, the steps of: treating said soil material to enhance or expand the removal of the arsenic from said soil material.

29. The process according to claim 28, wherein said treating is selected from the group consisting of chemical treatments, incineration, treatment with other plants, and treatment with micro-organisms.

30. A process for recovering an arsenic substance or concentrating an arsenic substance, which is present in a soil material, wherein said process comprises the steps of:

planting a fern plant of the family Pteridaceae on said soil material having arsenic as said arsenic substance;

wherein substantial concentrations of the arsenic substance accumulate within biomass of said fern plant solely by phytoremediation such that said fern plant removes said arsenic substance from said soil material.

31. The process according to claim 30, wherein said soil material further comprises an additional pollutant selected from the group consisting of trace elements, and metals.

32. The process according to claim 31, wherein said additional pollutant is gold.

33. The process according to claim 30, wherein said process further comprises at least one step selected from the group consisting of microbial treating, chemical treating and incinerating.

* * * * *

UNITED STATES PATENT AND TRADEMARK OFFICE
CERTIFICATE OF CORRECTION

PATENT NO. : 6,280,500 B1
DATED : August 28, 2001
INVENTOR(S) : Lena Q. Ma, Ken M. Komar and Elizabeth D. Kennelley It is certified that error appears in the above-identified patent and that said Letters Patent is hereby corrected as shown below:

<u>Title page,</u>
Item [74], should read as follows:
-- Brian S. Steinberger
  Law Offices of Brian S. Steinberger, P. A. --

Signed and Sealed this

Twenty-seventh Day of August, 2002

Attest:

Attesting Officer

JAMES E. ROGAN
Director of the United States Patent and Trademark Office